(12) United States Patent
Marbach

(10) Patent No.: US 6,571,117 B1
(45) Date of Patent: May 27, 2003

(54) CAPILLARY SWEET SPOT IMAGING FOR IMPROVING THE TRACKING ACCURACY AND SNR OF NONINVASIVE BLOOD ANALYSIS METHODS

(76) Inventor: Ralf Marbach, Kangasrinne 14, 90240 Oulu (FI)

( * ) Notice: Subject to any disclaimer, the term of this patent is extended or adjusted under 35 U.S.C. 154(b) by 69 days.

(21) Appl. No.: 09/925,380

(22) Filed: Aug. 10, 2001

Related U.S. Application Data

(60) Provisional application No. 60/224,533, filed on Aug. 11, 2000.

(51) Int. Cl.[7] ................................................. A61B 6/00
(52) U.S. Cl. ...................... 600/473; 600/310; 600/316; 600/476; 356/59
(58) Field of Search ............................... 600/473, 476, 600/310, 322, 316; 356/39, 354; 382/134

(56) References Cited

U.S. PATENT DOCUMENTS

| | | | |
|---|---|---|---|
| 5,941,821 A | * 8/1999 | Chou | 600/316 |
| 5,983,120 A | * 11/1999 | Groner et al. | 600/310 |
| 6,049,728 A | * 4/2000 | Chou | 600/316 |
| 6,104,939 A | * 8/2000 | Groner et al. | 600/322 |
| 6,278,889 B1 | * 8/2001 | Robinson | 600/322 |

* cited by examiner

*Primary Examiner*—Marvin M. Lateef
*Assistant Examiner*—Jeoyuh Lin

(57) ABSTRACT

The accuracy of noninvasive blood analysis methods is limited by the so-called tracking error. The correlation between the component concentration in the probed skin volume and the component concentration in the blood is improved by selecting particular locations on the patient's skin which provide a significantly higher density of capillary vessels than found on average (sweet spots). The higher capillary density causes the component concentration in the probed skin volume to better track the component concentration in the blood and as a useful side effect also improves the signal-to-noise ratio of the noninvasive measurement method itself. Methods for locating sweet spots and controlling the noninvasive measurement to selectively probe sweet spots are described. Also described are several embodiments of sweet spot imaging noninvasive measurement systems that integrate low-cost optical imaging of capillaries in the visible wavelength range with the high-accuracy noninvasive measurement in the component-specific, e.g., near-infrared, wavelength range.

22 Claims, 8 Drawing Sheets

CAPILLARY SWEET SPOT IMAGING FOR IMPROVING THE TRACKING ACCURACY AND SNR OF NONINVASIVE BLOOD ANALYSIS METHODS

CROSS-REFERENCE TO RELATED APPLICATIONS

This application is entitled to the benefit of Provisional Patent Application Ser. No. 60/224,533 filed Aug. 11, 2000.

FEDERALLY SPONSORED RESEARCH not applicable

SEQUENCE LISTING OR PROGRAM not applicable

SEQUENCE LISTING not applicable

REFERENCES CITED

1. *Exceptional Returns: The Economic Value of America's Investment in Medical Research,* report by the Funding First initiative of the Mary Woodard Lasker Cheritable Trust, Washington, D.C., May 2000 (http://www.laskerfoundation.org/fundingfirst)
2. R. Marbach et al., *Non-invasive Blood Glucose Assay by Near-Infrared Diffuse Reflection Spectroscopy of the Human Inner Lip,* Appl. Spectrosc. 47, 875–881 (1993)
3. R. Marbach, *On Wiener Filtering and the Physics Behind Statistical Modeling,* to be published in the Journal of Biomedical Optics (accepted Jul. 6, 2001)
4. R. R. Alfano and S. G. Demos, *Imaging of Objects Based Upon the Polarization or Depolarization of Light,* U.S. Pat. No. 5,847,394 filed Aug. 28, 1996
5. Y. Maekawa et al., *Non-invasive Blood Analyzer and Method Using the Same,* U.S. Pat. No. 5,769,076 filed May 2, 1996
6. D. Hochman and M. M. Haglund, *Optical Imaging Methods,* U.S. Pat. No. 5,845,639 filed Nov. 11, 1994
7. R. Marbach and H. M. Heise, *Optical Diffuse Reflectance Accessory for Measurements of Skin Tissue by Near-Infrared Spectroscopy,* Appl. Optics 34, 610–621 (1995)

FIELD OF THE INVENTION

The invention relates to methods and apparata for improving the tracking accuracy and signal-to-noise ratio of noninvasive blood analysis methods.

BACKGROUND OF THE INVENTION

Recent years have seen significant efforts spent on developing methods that can analyze human blood noninvasively as well as with sufficient accuracy, speed, low cost, minimal discomfort to the patient, and at the point-of-care. The biggest market segment for noninvasive blood analyzers is the diabetes market, because the disease affects a significant fraction of the population and patients are required to perform regular and frequent measurements of their blood glucose concentration. The following discussion will therefore concentrate on glucose as the primary candidate to which this invention can be applied, however, this is only meant in an exemplary way since the invention can be applied equally well to noninvasive measurement methods of other blood constituents, e.g., urea.

A conservative estimate by this author is that >US$ 2 billion have been spent during the last decade on R&D expenses for an accurate noninvasive blood glucose monitor. The reason, of course, is the significant market size and the potential ease with which the existing fingerprick devices could be pushed out of the market by even a fairly expensive noninvasive monitor if only the noninvasive device was accurate enough. Government also has a strong interest in an accurate noninvasive monitor because of the expected decrease in diabetes-related health care costs, which are currently estimated at $92 billion annually in the US [1].

Many different methods for the non-invasive measurement of blood glucose and other blood components-have been proposed. Virtually all are based on optical measurement techniques, i.e., they measure changes in the, e.g., absorbance, scatter, fluorescence, emission, polarization, Raman scatter, or a combination of these effects; in a tissue as a function of the glucose concentration in the blood. Further differences come from the different proposed wavelength regions of the electromagnetic spectrum and locations on the body. Wavelength ranges proposed range from the ultraviolet ($\lambda$<400 nm) to the far infrared ($\lambda$>20,000 nm) and typical locations proposed include the volar forearm, lip, fingertip, ear lope, and eye. Many of the published claims must be judged with extreme caution, especially in cases when the basic physical relationships are unclear or when the published data is statistically grossly insufficient.

The most promising noninvasive methods are absorbance-based optical measurements performed in diffuse reflection geometry in the near-infrared wavelength region (NIR). Proof of the basic technical feasibility was published in 1993 [2]; however, accuracy was insufficient at about 50 mg/dL root-mean-square (RMS) of measurement error, which is about 3 times larger than the clinically required value. Surprisingly, almost 10 years and $2+billion later, accuracy has not improved substantially since. We will now disclose the reason behind the limitation to accuracy and then, in the descriptive part of this text go on and disclose a method and apparata to overcome it.

The following discussion will concentrate on NIR measurements because these methods have the best chances for commercial success and are therefore prime candidates to which this invention can be applied. However, again, this is not meant in an exclusive way. In fact, the invention can be applied equally well to other noninvasive measurement techniques, based on other optical or even non-optical methods, because the problem solved by the invention applies equally to all noninvasive measurement methods. In the following, whenever words like "optical spectrum," "optically probed skin volume" etc. are used, they are meant only in an exemplary way.

The accuracy of all non-invasive methods is affected by two types of error, viz. (a) the "spectral error" due to the noise generated by the hardware of the noninvasive device, its sampling interface, and the interfering spectra from the other blood and tissue components and (b) the "tracking error" generated by the fact that the glucose concentration in the probed skin volume is not perfectly correlated with the glucose concentration in the blood. The latter type of error occurs because the glucose concentration in the probed skin volume (PSV) is an average of the glucose dissolved in the interstitial fluid (ISF) and the glucose in the blood. The instantaneous glucose concentration in the ISF (ISFG) can be very different from the glucose concentration in the blood (BG) because of the complicated temporal and spatial relationships between glucose intake and transport, and insulin intake and transport, in the body of a diabetic.

The accuracy of all non-invasive methods is judged by comparison to a high-quality invasive method, which serves as a secondary standard and calibration reference to the noninvasive method. Thus, even if one assumed that both the spectral error of the noninvasive device was zero (i.e., it measured glucose in the PSV (PSVG) with 100% accuracy) and the error of the invasive standard device was zero (i.e., it measured BG with 100% accuracy) then there would still be the difference between the PSVG and the BG causing a difference between the two devices. This is the tracking error, which is counted as an "error" of the noninvasive device, because the value of the invasive reference method is assumed to be "true" by definition. A detailed description of how the tracking error and the spectral error interact and combine to affect the overall measurement accuracy has recently become available [3].

Describing the situation in terms of time functions, it can be said that ISFG is virtually always lagging behind BG when BG goes up. When BG goes down, however, the ISFG in diabetic patients can either be lagging or leading, depending on the status of the complicated push-pull mechanism that controls the ISFG in the PSV. The exact time relationship between BG and ISFG is unpredictable in diabetics and can not be described with just a single number for "lag time." If one were to plot typical daily time profiles of diabetic BG and ISFG into a single graph and ask people to visually estimate the average time offset, numbers as high as 1 hour would occur commonly, and 2 hours occasionally. Medical doctors are primarily interested in BG and not in ISFG because today's invasive methods measure BG. The bottom line is that in diabetics, ISFG does not track BG closely enough to allow any of today's noninvasive methods to achieve full clinical usefulness and to successfully pass comparisons with invasive methods.

The fact that many of today's NIR absorbance-based optical methods are limited by tracking error and no longer by spectral error, can be rigorously proven by using the theory published in [3] and is also evidenced by the fact that measurement precision (repeatability) is often much better than the overall long-term accuracy. In a nutshell, modern NIR methods have become good at measuring the wrong thing. In order to improve performance, it is therefore necessary to improve upon the measurement method itself, because further improvements to the hardware alone will have virtually no effect on the measurement accuracy a.k.a. clinical usefulness.

It is obvious that an invention that solves the glucose accuracy problem can also be applied to improve the accuracy of noninvasive measurements of other blood components. E.g., during treatment of a dialysis patient, one can measure his PSV-urea concentration noninvasively and in real-time, e.g., by NIR diffuse reflection spectroscopy. The invention disclosed below can be applied to improve the accuracy of the urea measurement for the exact same reason that was discussed above, viz., to improve the tracking accuracy between the urea concentration in the blood and the urea concentration in the optically probed skin volume.

Three further remarks are on order. First, the invention disclosed below can be used in conjunction with all noninvasive measurement methods, including existing ones. Important changes have to be made to existing pieces of noninvasive device hardware, however, to (1) optimize the existing hardware so it can realize the full potential of the accuracy advantage provided by this invention, see the detailed discussion below, and (2) to accommodate the additional apparatus necessary for this invention. Second, in order for this invention to provide an accuracy advantage, the noninvasive method that it is applied to must itself be limited by tracking error and no longer by spectral error. In other words, if your precision is not yet better than your accuracy, then adding this invention will not help you. Thirdly and most importantly, because the correlation coefficient between the PSVG and BG is low at typically 0.85, the accuracy is just starting to become a steep function of correlation coefficient. In other words, every little bit of improvement in correlation coefficient is just starting to really pay off.

SUMMARY OF THE INVENTION

This invention provides methods and apparata for improving the tracking accuracy and signal-to-noise ratio of noninvasive blood analysis methods. The correlation between the component concentration in the probed skin volume and the component concentration in the blood is improved by selecting particular locations on the patient's skin which provide a significantly higher density of capillary vessels than found on average ("sweet spots"). The higher capillary density causes the component concentration in the probed skin volume to better track the component concentration in the blood and, as a welcome side effect, also improves the signal-to-noise ratio (SNR) of the noninvasive measurement method itself.

Methods for locating sweet spots and selecting them for measurement are described. These methods are based on low-cost, real-time optical imaging apparatus using visible wavelengths, and work best when applied to particular locations on the body, viz., mucousas. Also described are several embodiments of sweet spot imaging noninvasive measurement systems that integrate the low-cost optical imaging of capillaries in the visible wavelength range, with the high-accuracy noninvasive measurement in the component-specific wavelength range, e.g., the near-infrared.

An important characteristic of the sweet spot method is its low added cost. This is due to two fortunate facts. First, there are ways to use mass-produced CCD or CMOS cameras to generate real-time capillary images of sufficient quality. And second, it is possible to locate sweet spots on the skin that are large enough to overcome the spatial resolution limit set by the optical scattering in the skin. In other words, because sweet spots with lateral sizes in the range from about 0.5 to 3 mm can be found, standard techniques as applied in existing noninvasive measurement methods, e.g., NIR diffuse reflection, can be modified to achieve sufficient spatial resolution to allow selective probing of sweet spots. Expensive methods for increasing the spatial resolution of the noninvasive measurement like, e.g., optical coherence tomography or time-of-flight gating, can be avoided.

DETAILED DESCRIPTION OF THE INVENTION

Figure 2:
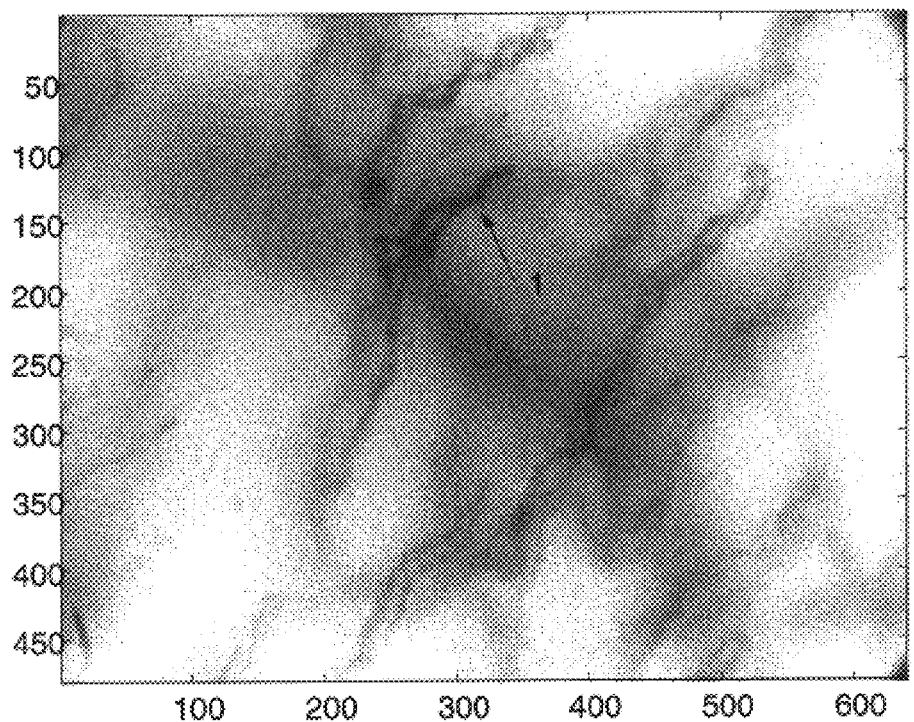
FIG. 2 shows an image of the lower inner lip in a region with average capillary density. Scale is 1.3 mm×1.0 mm.

The microvascular system inside the human skin is a complex network of small blood vessels located some 50–500 $\mu$m deep underneath the skin surface. FIG. 2 shows an image of the microvascular system in the lower inner lip in a region of average capillary density, i.e., a density typical for the lip. The capillaries 1, which are the smallest vessels with a diameter of about 6 $\mu$m, are located closest to the surface and their general direction of flow is normal to the surface, i.e., in unstretched skin, they typically come up towards the surface, take a sharp 180° turn at a depth of typically about 200 $\mu$m, and then go down again away from the surface whereby especially in diabetics the arterial and venous arms are often helically intertwined.

A first important conclusion from FIG. 2 is that, even in the lip, which is richly supplied with blood, the blood vessels occupy only a tiny fraction of the total volume of the tissue. Fortunately for all of us, blood components with small molecular weights can easily penetrate the capillary walls and diffuse through the interstitial fluid to the cells, e.g., glucose is the energy source for all cells. The glucose concentration in the skin volume probed by any noninvasive method is therefore a spatial average of the instantaneous glucose concentrations in the probed blood volume and the probed interstitial fluid volume.

This invention improves the accuracy of the noninvasive method by causing three beneficial effects. First, the ratio of probed blood volume to probed ISF volume is increased, which directly decreases tracking error. Second, the ISF volume still probed is now closer on average to nearby capillaries, which again directly reduces tracking error. And third, the signal-to-noise ratio (SNR) of the noninvasive measurement itself is improved, i.e., its spectral noise is reduced, because measurement sites are subject to a selection process and therefore look more similar to each other. The third effect is especially important when this invention is applied to the noninvasive measurement of blood constituents with large molecular weights, i.e., those that can not penetrate the capillary walls. Although this invention is primarily targeted at components with low molecular weight like, e.g., glucose, for which all three beneficial effects apply, the invention can also be applied to the measurement of high-weight components, e.g., proteins. For these the third effect is more important than for the low-weight components, because not only will it result in less spectral noise, but also in more spectral signal, resulting in a significant boost to overall spectral SNR.

The inner lower lip is a prime candidate for a noninvasive measurement site. Its technical advantages include the relatively high average capillary density compared to other skin; good temperature regulation; good protection against injuries; small variation of its optical characteristics between people; and the fact that near-perfect optical contact to a measurement probe can be made. As it turns out, there are two more, significant and hereto unknown, advantages, viz., the greatly reduced optical scattering in the lip mucousa allowing high-quality low-cost capillary imaging, and the fact that sweet spots can be found relatively easily in the lip.

Figure 4A:
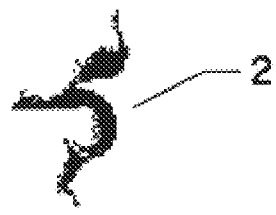
FIGS. 4a,b show sketches of the human lip and the approximate location of the sweet spot region.
Figure 4B:
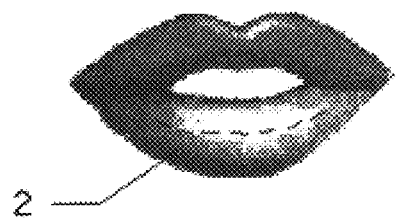
Figure 3:
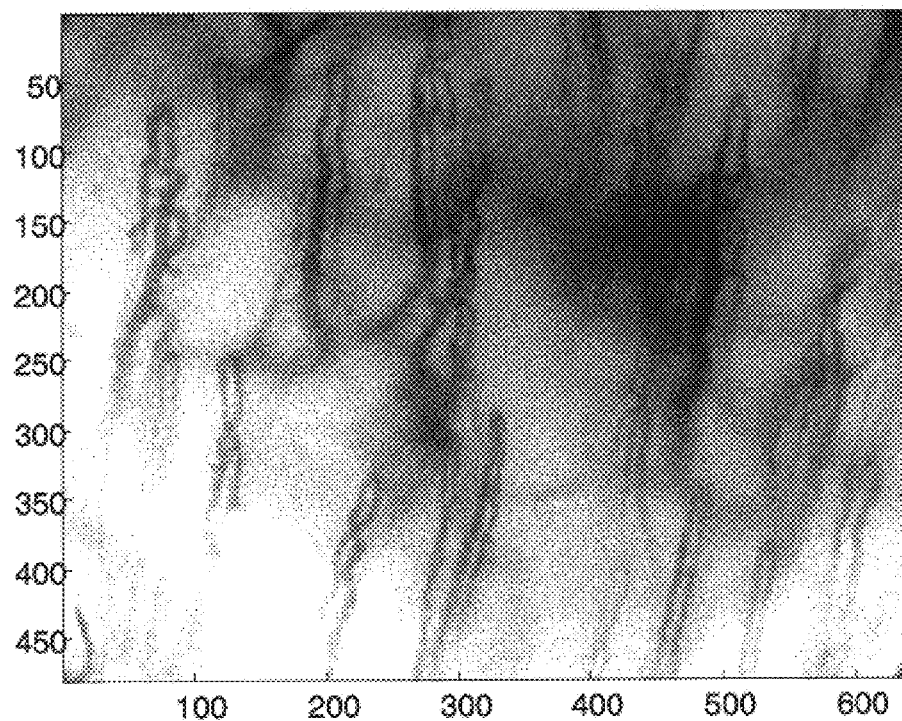
FIG. 3 shows an image of a "sweet spot" on the lower inner lip. Scale is 1.3 mm×1.0 mm.

FIG. 3 shows an image of a sweet spot on the lower inner lip. The sweet spot area covers the whole image and shows a capillary density roughly 3 times higher than in FIG. 2. Sweet spots can be easily found on the lip, because there is actually a whole sweet spot "region" located at the interface between the dry and the wet surface on the inner lower lip. (In the following discussion about the location on the lip, the words "inner," "inward" etc. indicate the direction along the lip's surface leading into the mouth and vice versa for the words "outer," "outward" etc. The directions into the mouth and parallel to the lip will also be referred to as the "vertical" and "horizontal" directions, respectively.) One can easily see the interface by simply pushing one's lower lip forward and looking into a mirror: there is a distinct color difference between the darker-red outer part (dry surface) and the pinker-red inner part (wet surface). The interface is a clearly defined line running across the whole width of the lip and it occurs where the lower lip seals against the upper lip when closing the mouth. FIG. 4 shows sketches of the human lip and the approximate location of interface line 2. Increased capillary density (ICD) is found in a narrow region along, and on both sides of, interface line 2. The vertical width of the ICD region is about 3–4 mm and is roughly centered on interface line 2. The whole ICD region could be used for sweet spot measurements. For practical reasons, however, the part located on the wet inner side of interface line 2 is preferred for the technical reasons mentioned above; and horizontally, the part located near the center of the lip is preferred for the practical reason of a patient's ease to make contact to a measuring probe.

In previous measurements on the lip [2] measurements were taken about 10+ millimeters inwards from interface line 2 so that the ICD advantage was not realized in these experiments.

The main requirements for a method to locate sweet spots are low-cost; possibility to integrate with existing noninvasive methods and apparata; and real-time capability (defined here as a time resolution of at least about 20 Hz). CCD or CMOS cameras mass-produced for consumer video applications can best meet these requirements. Most imaging methods currently being used or proposed to gather images from inside biological tissues with the required spatial resolution on the order of a few micrometers, are very expensive, complex, bulky, and slow, e.g., the various methods of confocal spectroscopy or optical coherence tomography. Straightforward optical imaging by shining visible light onto the skin and imaging the skin onto a CCD camera, does not work either because of two main problems, viz., diffuse reflections off the skin surface and optical scatter in the bulk of the skin. Fortunately, however, sweet spot detection only requires imaging of shallow capillaries or capillary tips, so that the effect of bulk scatter is not as severe as in other applications and can be reduced to tolerable levels using low-cost, real-time hardware. This statement is especially true for mucousas, which have significantly reduced bulk scatter when compared to normal, i.e., dry, skin. The bottom line is that capillary images of sufficient contrast quality can be produced at very low cost provided only that the effect of skin surface reflections can be reduced. Various methods to achieve this have been published, e.g., the use of crossed polarizers [4]; illumination at an angle inclined to the macroscopic surface normal to direct most of the surface reflection away from the entrance pupil of the imaging lens [5]; or the subtraction of consecutively measured images from each other to isolate only the moving structures inside the skin, i.e., blood [6]. Further technical details about these various capillary-imaging methods can be found in the cited references.

However, there is another, superior low-cost imaging method which can beat the others mentioned above in both price and performance. The method works by illuminating an annular pattern with a dark center on the skin and imaging only the "dark" center onto the camera. This annular-illumination method is favored by this author because it is very effective in reducing stray light from the skin surface; avoids polarizers and the associated light loss; requires no elaborate signal processing; requires a minimum of optical components and alignment; allows real-time display on standard TV monitors; and is also good at reducing the effect of bulk scatter in the image, by not giving the high-intensity illumination light any chance to directly scatter back into the camera. More detail will be given below in the discussion of various exemplary embodiments of sweet spot imaging noninvasive measurement (SSINIM) systems. Suffices to say here that a prototype imaging apparatus using the annular-illumination method can be built for <$300 parts (excluding the TV monitor) even in single quantity.

FIGS. 1 show an embodiment of an SSINIM system based on NIR diffuse reflection of the lower inner lip. The apparatus shown in FIG. 1a is based on the apparatus used in the prior lip measurements [2,7] but modified and with capillary-imaging apparatus added. The noninvasive method is based on an FTIR spectrometer (not shown) as a source of modulated NIR light 3. In the original device, collimated NIR light 3 is focused via off-axis parabolic mirror 4, plane mirror 5, Axicon mirror pair 6 and 7, and hemispherical $CaF_2$ lens 8, onto surface 9 of skin 10 of the lip. A fraction of light 3 is then diffusely reflected by skin 10, collected by ellipsoidal mirror 11, and directed to NIR detector 12. Particular advantages of the design include the large collection efficiency of the diffusely reflected radiation, and the relatively high patient comfort since the device is specifically designed for lip measurements.

Figure 1A:
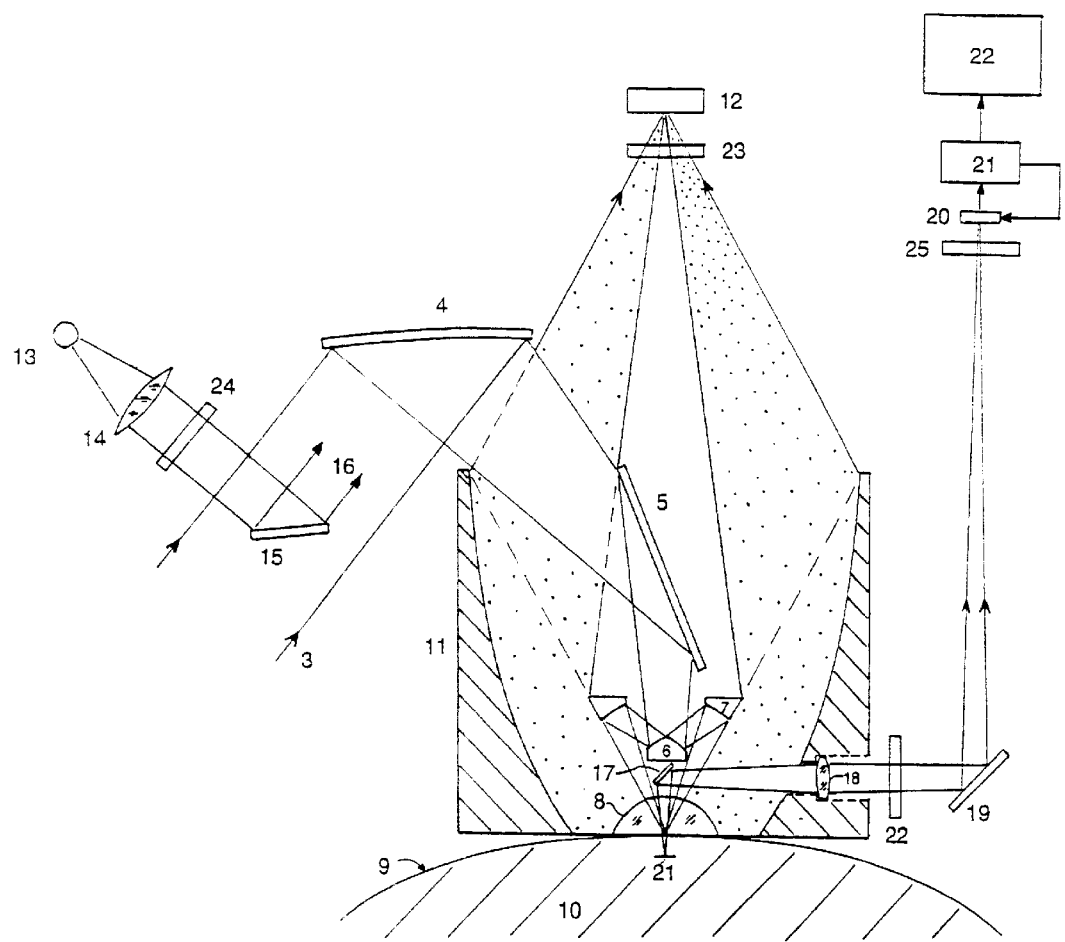
FIGS. 1a–d show a first embodiment of the sweet spot imaging technique applied to an existing noninvasive measurement method based on near-infrared diffuse reflection of the lip using a Fourier-transform spectrometer.

Three steps are necessary to upgrade an existing piece of noninvasive measurement hardware into a complete SSINIM system. The first step is to add capillary imaging apparatus, and one possible way is shown in FIG. 1a. Light source 13 emits visible light 16 which is collimated by lens 14 and re-directed by plane mirror 15 to be collinear with measurement light 3. The preferred wavelength range of imaging light 16 is a bandpass centered around 550 nm with a bandwidth of several ten to one hundred nanometers, because capillary image contrast is maximized at the peak absorbance wavelength of the hemoglobin in the blood vessels. Since the noninvasive measurement uses near-infrared light 3 with wavelengths >1000 nm, the imaging and the actual noninvasive measurement take place in separate, non-overlapping wavelength ranges. Light source 13 can be a green LED, or can be a tungsten-halogen or metal-halide lamp of approximately 5–25 Watt lamp wattage and equipped with a green bandpass filter (not shown). Imaging light 16 and measurement light 3 then travel alongside each other to skin surface 9. An optional optical filter 23 in front of photodetector 12 passes infrared light 3 but blocks visible light 16, in order to reduce the quantum noise generated in detector 12. Conversely, optional optical filter 22 blocks infrared light 3 but passes imaging light 16 on towards CCD or CMOS camera 20, in order to increase the contrast of the capillary image by "puryfying" the 550 nm imaging light. The imaging optics is relatively simple and consists of two folding mirrors 17 and 19, and a lens 18 housed in a circular opening in the side of mirror 11. Camera 20 receives power supply and exposure and/or gain control signals from electronic base unit 21. Unit 21 also amplifies the camera output, which can be a standard composite video signal, and feeds it into monitor 22, which can be a standard, miniature, monochrome, TV set. Particular advantages of the arrangement shown in FIG. 1a are that (1) the imaging optics has virtually no effect on the efficiency of the NIR measurement, since it is located in the "un-used" solid angle, and (2) the imaging optics does not spatially interfere with the patient performing the lip measurement.

Lens 18 images the photosensitive area of camera 20 into an entrance field 21 in skin 10. The focus depth, defined here as the vertical distance between skin surface 9 and entrance field 21, can be set at a fixed value of about 250 $\mu$m or, preferably, is user-adjustable from approximately zero to 500 $\mu$m in order to accommodate variations in vessel location between people and also to provide optional three-dimensional depth scanning information to the user. Focus depth adjustment under user control can be realized by providing mechanical, or preferably electro-mechanical, means to move, e.g., lens 18 or camera 20, in the direction of the optical axis of the imaging optics. Lens 18 is preferably a doublet and has optical magnification such that that the image of a single red blood cell (RBC) extends over at least three camera pixels. The typical size of an RBC is about 6 $\mu$m. E.g., if a ⅓" format CMOS camera with 640×480 pixels and pixel size of 8 micrometer square was used, then a suitable value for the optical magnification of lens 18 would be four, because then the size of a pixel's image in the plane of entrance field 21 is 2 $\mu$m square, i.e., one third of an RBC. In this case, the size of entrance field 21 would be 1.28 mm by 0.96 mm, which is sufficient to enable the user to quickly locate sweet spots in his lip.

Figure 1B:
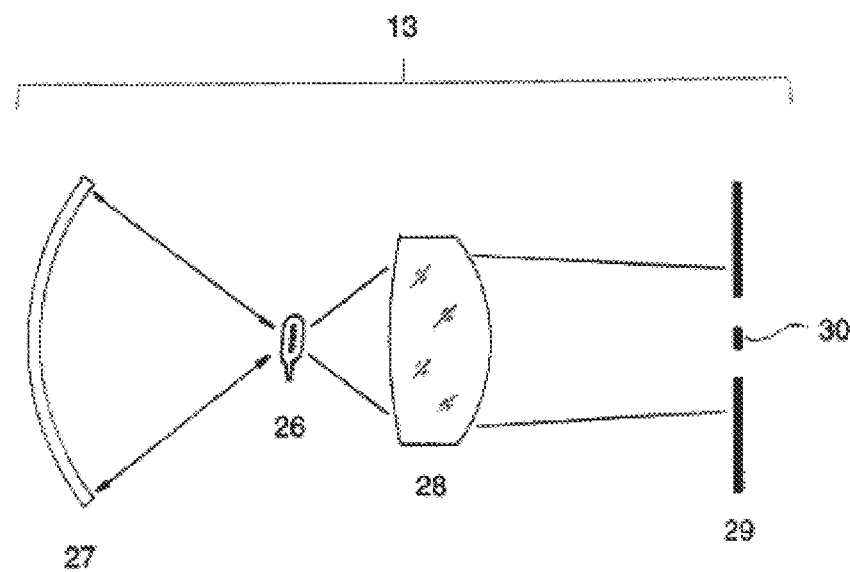
Figure 1C:
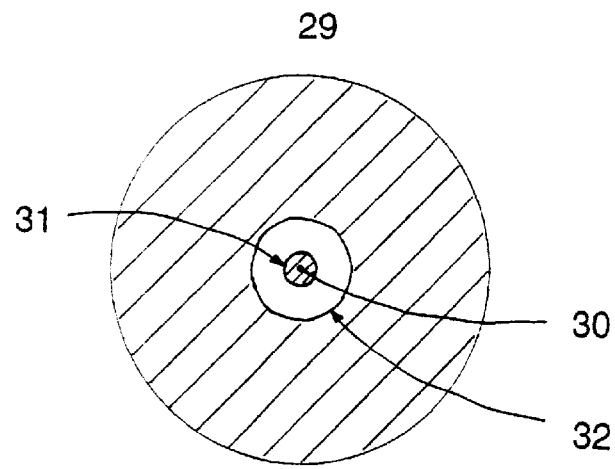
Figure 1D:
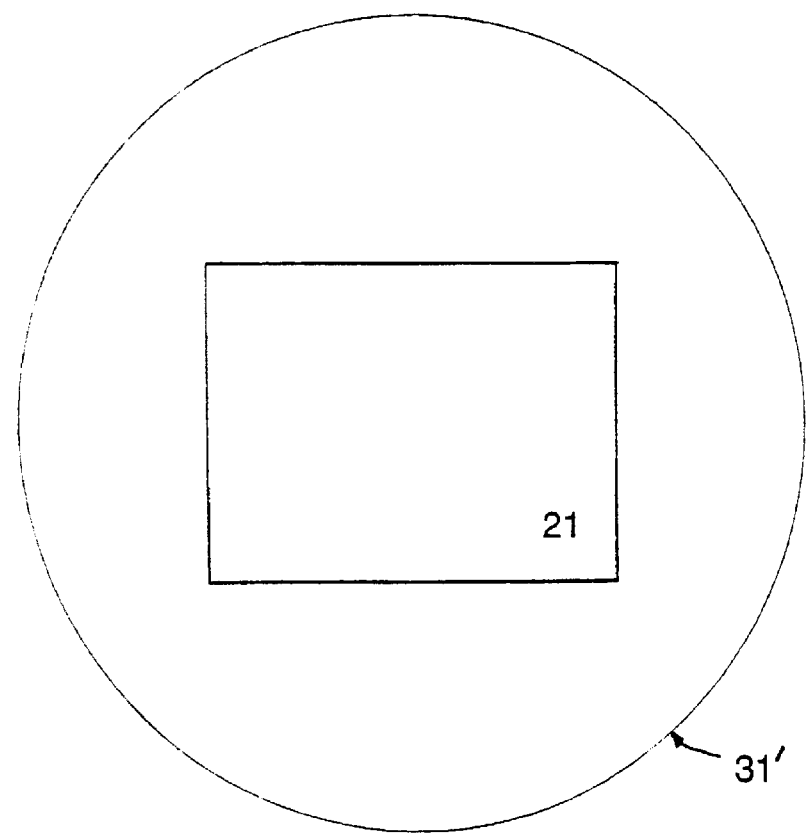

Image contrast can be improved by using any of the methods described in Refs [4,5,6]. Solid-angle separation [5] is automatically used in FIG. 1a, and optional crossed polarizers 24 and 25 can be used to further increase contrast. However, the preferred way to improve contrast is by illuminating an annulus on skin surface 9 and then imaging the "dark" center of the annulus onto camera 20. To this end, light source 13 may be built as shown in FIG. 1b where light bulb 26, mirror 27, condenser lens 28 and field stop 29 with dark center 30 are shown. The annular opening of field stop 29 has inner diameter 31 and outer diameter 32 (cmp. FIG. 1c), which when imaged into the plane of entrance field 21, become diameters 31' and 32', respectively. Continuing the previous example, diameter 31' should be approximately 2.5 mm, i.e., slightly larger than the 1.6 mm diagonal of entrance field 21 (cmp. FIG. 1d). Outer diameter 32' (not shown) of the light annulus can be as large as about 8 mm and still contribute to the image brightness. Because the focus depth is small, viz., a few hundred $\mu$m, in practice it does not matter whether imaging light 16 from source 13 is focussed at the plane of entrance field 21 or at skin surface 9. The practical goal is to prevent surface reflections off of skin surface 9 to directly scatter back into imaging lens 18, and if the geometry of entrance field 21 and illumination inner diameter 31' is as shown in FIG. 1d, or similar, then the separation between illuminated and reflected light 16 is large enough and high-contrast images can be obtained.

The second, very important step is to adjust the existing noninvasive measurement hardware to be able to achieve the full accuracy advantage provided by this invention. In the original setup [2,7] photodetector 12 was a Ø4 mm InSb photodiode. The size of the spot on skin surface 9 from which measurement light 3 was detected, was thus approximately Ø3 mm corresponding to the "image" of photodetector 12 formed by mirror 11 on skin surface 9. (The image formed by ellipsoidal mirror 11 is severely aberrated but an effective magnification can still be specified [7].) A Ø3 mm spot size on the skin is too large to selectively probe sweet spots reliably, and the diameter of photodetector 12 should therefore be decreased by about 50%, so that a spot size of about ⌀1.5 mm or smaller is probed on skin 10. Two remarks are on order. First, in the sweet spot method, one can still average over a large skin area, but only by selecting multiple sweet spots and averaging over them, and not by unselectively including skin areas of lower capillary density. And second, because the average lateral size of the "banana-shaped" path taken by a diffusely reflected photon in skin 10, is only on the order of 0.3 mm in the NIR, a ⌀1.5 mm spot size on the skin is effectively only probing photons that have spend their entire "lifetime" in the skin in the sweet spot area. In other words, the chance that a detected photon has travelled much of its path in skin 10 through outside areas of lower capillary density, and then has diffused into the sweet spot area, is virtually zero.

In order to enable imaging using the annular-illumination method as shown in FIG. 1b, another change necessary to the particular piece of noninvasive measurement hardware [7] is to replace the original Axicon-type mirrors 6 and 7 with a conventional, imaging-type pair of mirrors, e.g., a Schwarzschild objective.

The third step is to change the existing measurement process to integrate the sweet spot selection and the noninvasive measurement into one measurement process. A simple way to achieve this is by placing the TV monitor 22 into the field of view of the patient while he is doing the lip measurement. The process is then simply as follows: The patient presses his inner lower lip against the optical interface of the probe, i.e., lens 8, and views real-time images of the contacted skin area on TV monitor 22. The patient moves skin 10 of his lip until a sweet spot area appears in the image, at which time he presses a start button to initiate the noninvasive measurement. While seemingly primitive, this process is extremely reliable since the learning curve on sweet spot detection is rapid (minutes) and very simple. Various optical and/or acoustical feedback signals can be provided to the patient to inform him about the status of the measurement, and also to give him the option to cancel out of a measurement. Alternatively, using modern microprocessors, it is also possible to have real-time image analysis software identify sweet spots and either initiate the noninvasive measurement automatically in software, or at least inform the patient that a sweet spot has been found.

One important requirement for any SSINIM hardware is that the position of entrance field 21 of imaging light 16 is precisely controlled relative to the position of the skin volume probed by measurement light 3. However, the two areas do not necessarily have to be identical, nor do they have to be rigidly fixed with respect to each other, as shown in the following two exemplary embodiments of SSINIM systems.

Figure 5A:
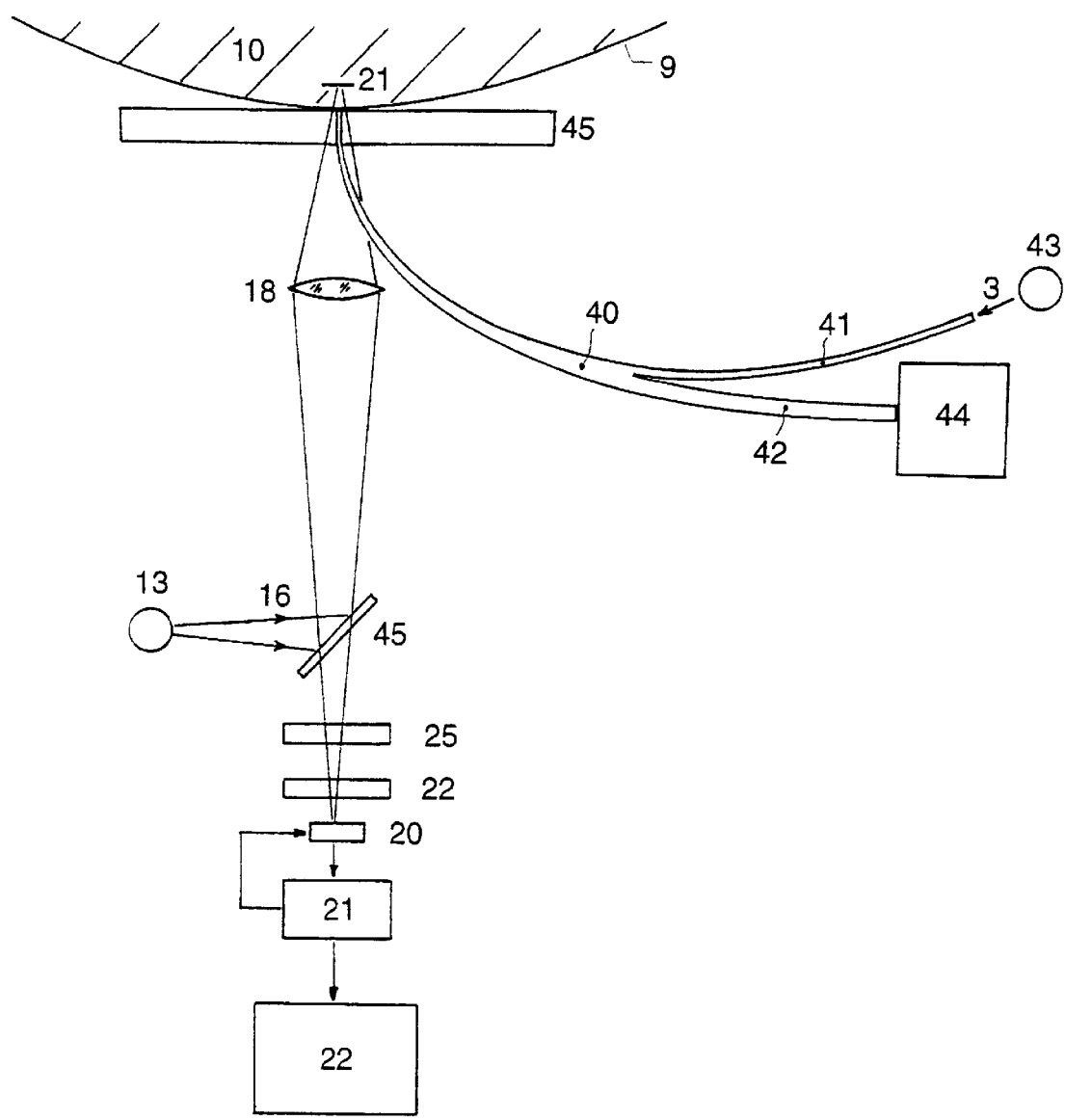
FIGS. 5a,b show a second embodiment of the invention where the sweet spot imaging technique is applied to noninvasive methods using a fiber optic probe.
Figure 5B:
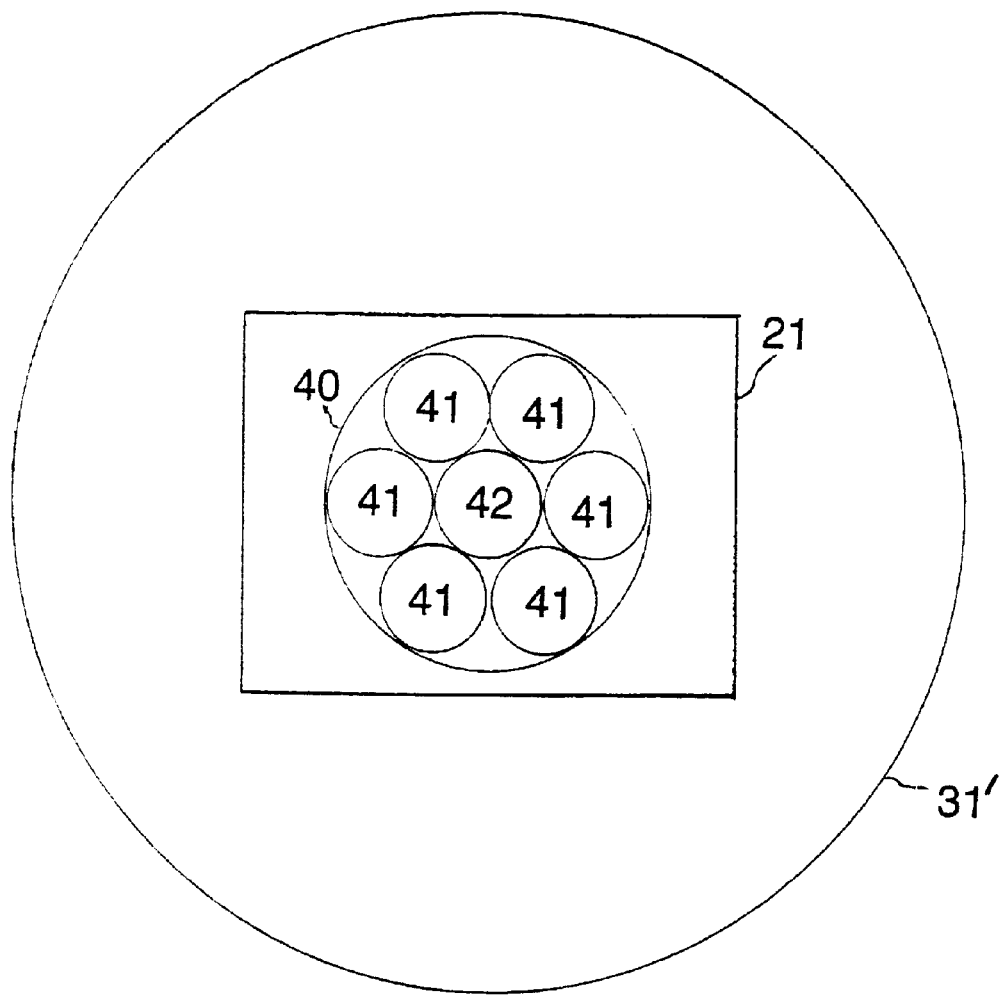

In FIG. 5a an example of an arrangement based on a bifurcated fiber bundle 40 and an optical window 45 is shown. At the skin end, bundle 40 is arranged as shown in FIG. 5b with six illumination fibers 41 surrounding one pickup fiber 42. Illumination fibers 41 transport measurement light 3 coming from light source 43 to skin 10 of, e.g., the lip. Pickup fiber 42 transports measurement light 3 that has been diffusely reflected by skin 10 to the spectroscopic analyzer unit 44, where the light is spectrally dispersed, detected, amplified, digitized, and the spectrum recorded in computer memory. A typical cladding diameter of fibers 41 and 42 is in the range from 200–500 μm, thus making the overall diameter of the six-around-one geometry of fiber bundle 40 smaller than approximately 1.5 mm. Illumination fibers 41 are typically high-NA fibers, e.g., FT-400-URT from 3M Optical Transport Systems, and pickup fiber 42 is typically a high-quality fused silica fiber with NA=0.22.

Capillary imaging is integrated by imaging an entrance field 21 that is larger than, and includes and surrounds, the diameter of the fiber bundle 40, as illustrated in FIG. 5b. The image detected by CCD or CMOS camera 20 will therefore be dark in the center, and capillaries will only be seen in areas near the edges of the image. Two remarks are on order. First, the arrangement only works if the size of the sweet spot is larger than the diameter of the fiber bundle 40, and this is why the sweet spot region on the lip is a prime candidate for this measurement. Second, depending on the diameter of fiber bundle 40 and the required spatial resolution of the image, camera 20 may need to have more pixels than the 640×480 VGA format. If the resolution is kept at the previously discussed level with each pixel corresponding to an area of approximately 2 μm square in entrance field 21, then the size of entrance field 21 may be insufficient. In this case, one can reduce the image resolution slightly to, say, 3 μm square per pixel, and/or select a camera with more pixels, e.g., one with 1280×720 HDTV format.

Other components shown in FIG. 5a were already described in the discussion of FIG. 1, with the exception of the beamsplitter 45, which re-directs imaging light 16 to skin 10, and passes imaging light 16 on its return path to camera 20. Image contrast is preferably increased by forming imaging light source 13 as shown in FIG. 1b, i.e., by using annular-illumination. Alternatively or additionally, beamsplitter 45 may be a polarizing beamsplitter and a crossed polarizer 25 (used as an analyzer) may be positioned in front of camera 20.

The measurement process is similar to the one described above, with the only exception that the user watches images with a central dark area on TV monitor 22, and starts the noninvasive measurement when he sees that the central image area is fully surrounded by sweet spot area. As described above, focus depth adjustment under user control is a valuable option that can also be realized in the apparatus shown in FIG. 5, e.g., by moving lens 18 along its optical axis.

A multitude of noninvasive measurement methods are based on bifurcated fiber bundles, and the particular fiber geometry shown in FIG. 5 is fairly typical for instruments working in the near-infrared spectral range. However, actual fiber bundles employed in existing instruments may differ in a number of ways from the illustrated one. FIG. 5 is therefore only meant as an example, to show the general arrangement in which the sweet spot imaging method can be integrated into a noninvasive measurement probe based on a fiber bundle.

Figure 6:
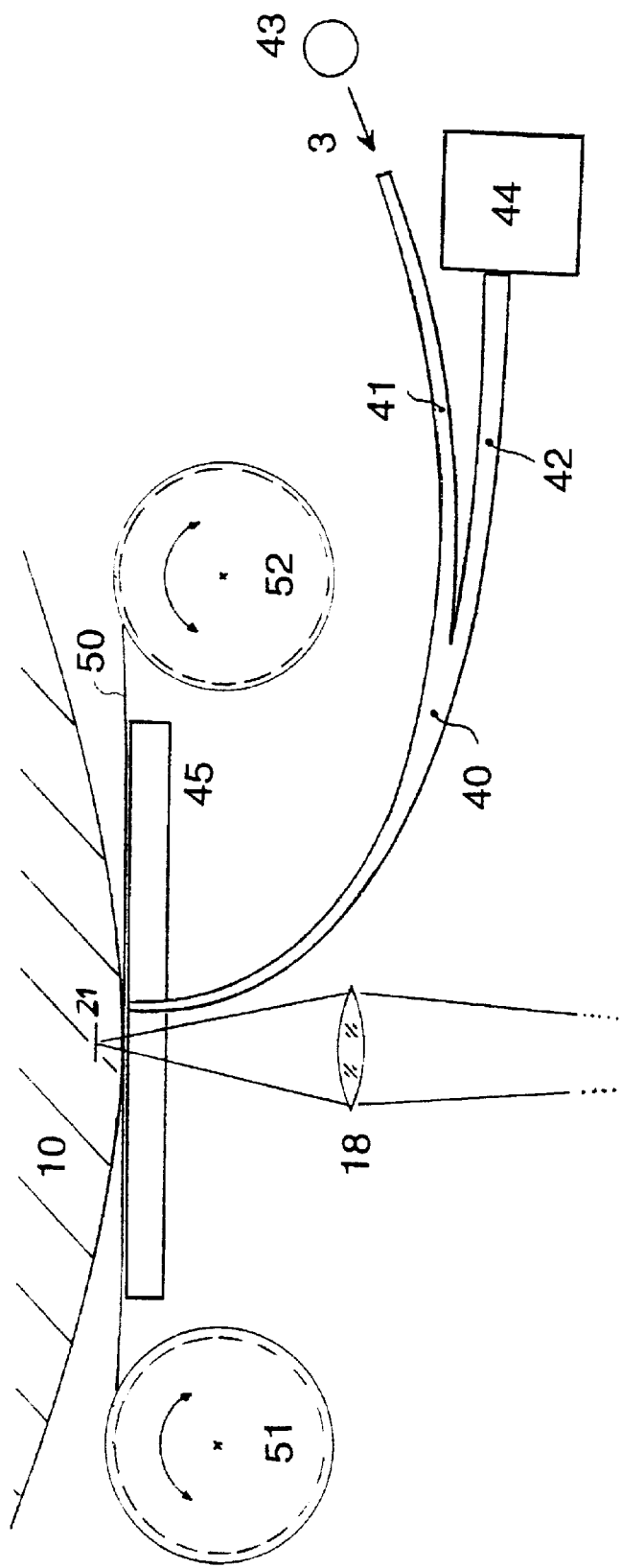
FIG. 6 shows a third embodiment of the invention where the sweet spot imaging technique is applied to noninvasive methods using a fiber optic probe and a movable foil.

FIG. 6 shows another example of an SSINIM system based on a fiber bundle 40. The arrangement is similar to the one shown in FIG. 5 but with one valuable addition. In FIG. 6, skin 10 does not make direct contact with optical window 45 but the two are separated by a thin plastic foil 50 made from, e.g., PE or PTFE, and with a thickness of preferably <50 μm. Foil 50 is wound onto spools 51 and 52 and can be moved relative to window 45 as indicated by the arrows. There are three main purposes of foil 50. First, when used in a disposable fashion, it can provide a sterile probe interface, which is especially important in cases where the system is used by multiple patients. In this case, spools 51 and 52 preferably would also be disposable with one being the feeder spool and the other the collector spool, and both spools being driven electro-mechanically and controlled by a computer to ensure proper incrementation. Second, the foil can be used to drag skin 10 of the lip across window 45, i.e., it can help the user to locate and position sweet spots. To this end, the foil would preferably advance back and forth in the "vertical" lip direction (defined above), because this direction is harder to control by the user than the "horizontal" direction parallel to the lip. In the ideal case, a horizontal drive could also be added (not shown in FIG. 6) and both directions driven under user control with a joystick interface. In any case, the total travel of foil 50 should be smaller than roughly ±5 mm in either direction in order to minimize stretching of the skin. Also, the mechanical drive(s) need to be able to advance in small, precise increments on the order of 50 μm or smaller. The third purpose is that foil 50 allows to overlap entrance field 21 and the PSV spatially, yet sequentially in time. This is done by initially positioning entrance field 21 and the probing end of fiber bundle 40 off-center from each other, as shown in FIG. 6, in order for the user to get an unobstructed view of the capillary image first. Once the user has located a sweet spot and initiated the noninvasive measurement, spool 52 is wound up, and skin 10 is dragged along, a distance equal to the initial distance between entrance field 21 and fiber bundle 40.

One particular modification is to replace foil 50 with a net. The image information from camera 20 can be used in a closed-loop fashion to position the net, and the lip sticking to it, in such a way that sweet spots are measured with minimum interference from the material of the net.

Figure 7:
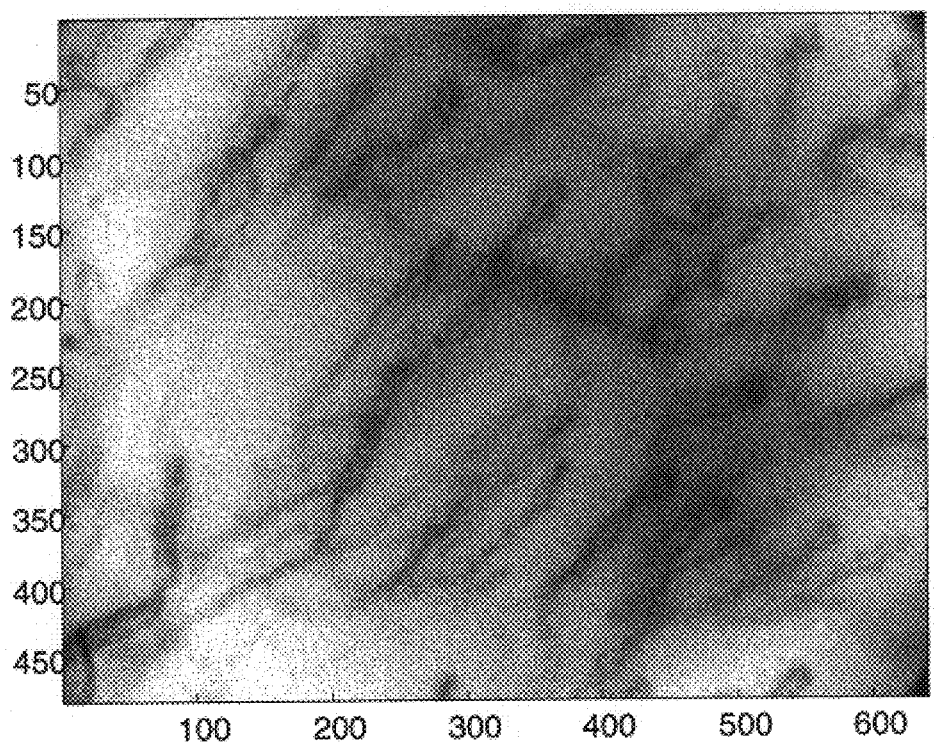
FIG. 7 shows an image of a "sweet spot" on the inner side of the cheek. Scale is 1.3 mm×1.0 mm.

FIG. 7 shows a capillary image of a sweet spot on the inner side of the cheek. The cheek is also very well capillarized, and sweet spots can be easily found if areas close to the mouth are searched. A disadvantage of the cheek is limited accessibility, however, this can be overcome by designing the sampling interface to fit into a tube with outer dimensions of, e.g., 2" long and ⅓" diameter, which be relatively easily done with the probe heads shown in FIGS. 5 and 6.

Figure 8:
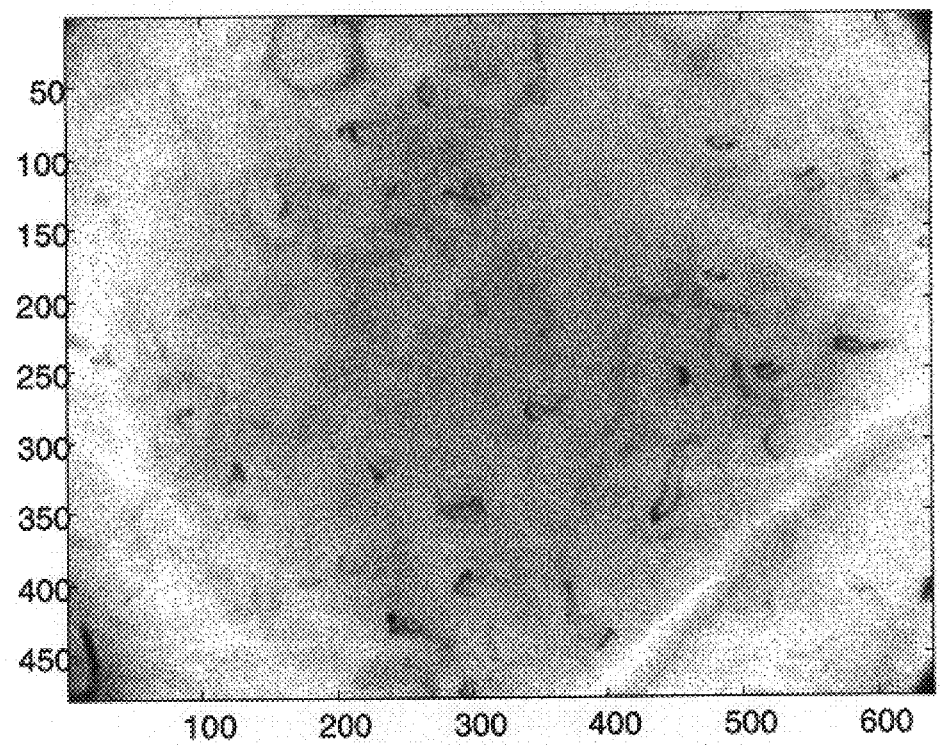
FIG. 8 shows an image of the capillaries in the volar forearm. Scale is 1.3 mm×1.0 mm.

FIG. 8 shows a capillary image of the volar forearm. This picture is provided for comparison to FIGS. 2, 3, and 7; and it shows that the capillary distribution in the arm is also not uniform. Whereas the central area of FIG. 8 is relatively poor in capillaries, higher capillary density is present in parts of the lower right area. Thus, sweet spot imaging is also helpful to improve the tracking accuracy of noninvasive measurement methods probing the forearm.

One particular modification to the sweet spot imaging method is to use a "non-imaging" method to locate sweet spots. "Non-imaging" here is a misnomer, because some spatial resolution is still provided, however, only on the order of several hundred μm to one millimeter, i.e., much coarser than the true imaging methods based on CCD or CMOS cameras described above. We will call these methods "coarse imaging" in the following. Examples of coarse-imaging methods are the measurement of skin color or the measurement or blood flow using laser doppler. The first method would detect, e.g., the interface line 2 between the dry outer lip and the wet inner part of the lip from the color difference, and could be based on commercially available miniaturized LED color sensors. Each sensor would measure the color of at least one spot on the skin, each spot being at least several hundred μm in diameter. Given the a-priori information about the geometry of the sweet spot region on the lip, one can easily design a 2-dimensional array of spots which, when the lip is contacted across it, allows the computation of the location of a sweet spot. The "grid spacing" between adjacent spots will typically be on the order of one millimeter. Alternatively, a very small number of spots could be used, e.g., three spots arranged in a triangle or just two arranged vertically, and the user could move his lip until the sweet spot is located. In practice, this is easy to do because the patient can just contact his lip low and then "slide up" until the color change is detected. Similar remarks about the geometry of the measurement spots also apply to a laser doppler blood flow measurement, which is basically a measurement of the amount and speed of the red blood cells in the tissue. The "true" imaging methods based on CCD or CMOS cameras described above, however, are tried and tested and are believed to be superior to the "coarse imaging" methods because of (1) greater reliability, (2) similarly low or even lower cost, and (3) the large amount of additional information provided to the user during the measurement.

Numerous variations and modifications to the enclosed embodiments are possible and are apparent to those skilled in the art. Currently, there are probably more than one hundred different noninvasive measurement systems in existence, and each one has probably multiple ways available as to how to integrate the capillary imaging apparatus and form a complete sweet spot imaging noninvasive measurement system. The particular embodiments shown are merely examples of the multitude of possible designs that can be used to reduce this invention to practice. Variations and modifications falling within the scope of the appended claims will be apparent to those skilled in the art. E.g., several CCDs or CMOS cameras 20 could be used simultaneously and their entrance fields 21 geometrically arranged in different ways around the noninvasive measurement probe head.

I claim:

1. An apparatus for improving the accuracy of a noninvasive blood analysis measurement instrument, comprising:
   A.) first means for locating at least one sweet spot on the skin, said sweet spots having a significantly higher density of capillaries than the average of the surrounding skin area;
   B.) second means for controlling the measurement process performed by said noninvasive instrument such that it selectively probes sweet spots;
   whereby the tracking error is reduced and the signal-to-noise ratio is increased and full clinical usefulness can be achieved.

2. The apparatus of claim 1 wherein said noninvasive instrument comprises a near-infrared spectrometer.

3. The apparatus of claim 1 wherein said skin is the inner lower lip.

4. The apparatus of claim 3 wherein said sweet spots are located close to interface line 2.

5. The apparatus of claim 1 wherein the lateral size of said sweet spots is at least about 0.3 millimeter.

6. The apparatus of claim 1 wherein said first means comprise an imaging apparatus including a photodetector array selected form the group consisting of CCD arrays and CMOS arrays.

7. The apparatus of claim 6, said imaging apparatus further including a light source and optical means to illuminate an annular pattern with a dark center on said skin.

8. The apparatus of claim 1 wherein said second means comprise a monitor to display real-time images of the capillaries in said skin and a button that the user has to press to start the noninvasive measurement process.

9. The apparatus of claim 1 wherein said second means comprise real-time image analysis means to automatically detect sweet spots and indicator means to signal this event to the user.

10. The apparatus of claim 1 wherein said second means comprise a movable foil 50 to position said skin relative to said noninvasive instrument.

11. The apparatus of claim 1 wherein said first means comprise color measurement means to measure the color of a plurality of skin spots, each of said skin spots being at least several hundred micrometers in lateral size.

12. The apparatus of claim 1 wherein said first means comprise laser Doppler measurement means to measure the blood flow of a plurality of skin spots, each of said skin spots being at least several hundred micrometers in lateral size.

13. A method for improving the accuracy of a noninvasive blood analysis measurement instrument, comprising the steps of:

A.) locating at least one sweet spot on the skin, said sweet spots having a significantly higher density of capillaries than the average of the surrounding skin area;

B.) controlling the measurement process performed by said noninvasive instrument such that it selectively probes sweet spots;

whereby the tracking error is reduced and the signal-to-noise ratio is increased and full clinical usefulness can be achieved.

14. The method of claim 13 wherein said noninvasive instrument comprises a near-infrared spectrometer.

15. The method of claim 13 wherein said skin is the inner lower lip.

16. The apparatus of claim 15 wherein said sweet spots are located close to interface line 2.

17. The method of claim 13 wherein said step of locating at least one sweet spot is comprised of A.) forming an annular illumination pattern with a dark center on surface 9 of said skin; and B.) imaging an entrance field 21 located laterally within said dark center and at a shallow depth underneath said surface 9 onto a camera 20.

18. The method of claim 13 wherein said step of locating at least one sweet spot is comprised of measuring the color of a plurality of skin spots, each of said skin spots being at least several hundred micrometers in lateral size.

19. The method of claim 13 wherein said step of locating at least one sweet spot is comprised of measuring the laser Doppler signal from a plurality of skin spots, each of said skin spots being at least several hundred micrometers in lateral size.

20. A method for improving the accuracy of a noninvasive blood analysis measurement instrument, comprising the steps of:

A.) providing means for limiting the lateral size of the skin volume probed by said noninvasive instrument to a predetermined value;

B.) locating a sweet spot on the skin, said sweet spot having a significantly higher density of capillaries than the average of the surrounding skin area and a lateral size at least as large as said predetermined value;

C.) positioning said skin relative to said noninvasive instrument such that the skin volume probed by said noninvasive instrument is overlapped by sweet spot area; and D.) starting a measurement on said noninvasive instrument;

whereby the tracking error is reduced and the signal-to-noise ratio is increased and full clinical usefulness can be achieved.

21. The method of claim 20 wherein said step of providing means for limiting the lateral size comprises providing a fiber bundle guiding the measurement light.

22. The method of claim 20 wherein said step of positioning said skin comprises providing a movable foil 50 to move said skin relative to an optical window 45.

* * * * *